US00PP37786P3

(12) United States Plant Patent
Grosser

(10) Patent No.: US PP37,786 P3
(45) Date of Patent: Oct. 20, 2026

(54) SWEET ORANGE PLANT NAMED 'OLL-DC-3-40'

(50) Latin Name: *Citrus sinensis*
Varietal Denomination: OLL-DC-3-40

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/381,483

(22) Filed: Nov. 6, 2025

(65) Prior Publication Data

US 2026/0130302 P1 May 7, 2026

Related U.S. Application Data

(60) Provisional application No. 63/717,571, filed on Nov. 7, 2024.

(51) Int. Cl.
*A01H 5/08* (2018.01)
*A01H 5/02* (2018.01)
*A01H 6/78* (2018.01)

(52) U.S. Cl.
USPC ..... Plt./202
CPC ..... *A01H 6/785* (2018.05); *A01H 5/02* (2013.01); *A01H 5/08* (2013.01)

(58) Field of Classification Search
USPC ..... Plt./202
CPC . A01H 5/08; A01H 5/00; A01H 6/785; A01H 6/78
See application file for complete search history.

(56) References Cited

U.S. PATENT DOCUMENTS

PP26,087 P3 11/2015 Grosser
PP27,277 P3 10/2016 Grosser

OTHER PUBLICATIONS

Grosser et al. Keeping Florida Citrus Growers Informed, UF/IFAS Citrus Research Summaries, Aug. 2023, 1-3, 72. (Year: 2023).*

* cited by examiner

*Primary Examiner* — June Hwu
(74) *Attorney, Agent, or Firm* — Koenig IP Works, PLLC; Katherine Koenig

(57) ABSTRACT

A new and distinct cultivar of sweet orange plant named 'OLL-DC-3-40' selected for processing and fresh market, characterized by an increased tolerance to HLB. Fruit of 'OLL-DC-3-40' are round, and trees of 'OLL-DC-3-40' are large and display quick growth.

10 Drawing Sheets

Genus and species: *Citrus sinensis.*
Cultivar denomination: 'OLL-DC-3-40'.

ACKNOWLEDGEMENT OF FEDERAL RESEARCH SUPPORT

N/A.

BACKGROUND OF THE NEW CULTIVAR

The present invention relates to a new and distinct cultivar of sweet orange, botanically known as *Citrus sinensis*, and hereinafter referred to by the name 'OLL-DC-3-40'. *Citrus sinensis* is a member of Rutaceae.

The new sweet orange cultivar 'OLL-DC-3-40' is a nucellar seedling selected from a population of over 214 nucellar seedlings grown from seed derived from previously released sweet orange cultivar 'OLL-8' (U.S. Plant Pat. No. 26,087), from an OLL (Orie and Louise Lee) series of sweet oranges. The mother plant 'OLL-8' is a somaclone regenerated from embryogenic callus (tissue culture) of the original unstable OLL sweet orange, with high quality fruit that usually matures in the standard 'Valencia' time period (not patented). The 'OLL-8' nucellar seedling population was planted in Dade City, Florida, in April of 2012, and all trees were planted on their own roots (no grafting). After four years in the ground, the commercial grove was devastated by huanglongbing (HLB), or *Citrus* greening, and the grove was sold for real estate development. Thus, in spring of 2016, the entire population was assessed for HLB, and 'OLL-DC-3-40' was one of only two clones that were identified as having no HLB symptoms. Trees were still completely juvenile at this time, showing typical upright growth and thorniness, and the trees were not yet fruiting. Both selected trees tested negative for CLas using qPCR (the only two clones to do so), but this was unexpected because the entire population of trees were vigorously growing trees with lots of new vegetative flush to attract psyllids, and there was plenty of CLas inoculum in the adjacent collapsing commercial blocks. This suggested some higher level of HLB tolerance or possibly resistance. 'Valencia' is considered to be the "gold standard" of processing oranges worldwide; however, OLL oranges produce juice with better color and almost always better flavor.

SUMMARY OF THE INVENTION

The new sweet orange cultivar 'OLL-DC-3-40' has not been observed under all possible environmental conditions.

The phenotype of the new cultivar may vary with variations in environment and cultural practices such as temperature, light intensity, fertilization, irrigation, and application of plant growth regulators without any change in genotype.

The new sweet orange cultivar 'OLL-DC-3-40' produces round oranges with internal and external color similar to that of 'Rhode Red Valencia' (not patented). True-to-typeness of 'OLL-DC-3-40' was provided by reset trees on super-root mutant 'UFR-1' (U.S. Plant Pat. No. 27,277) clone #28 and 'UFR-1' clone #55 rootstocks, with 3.5-year-old trees (HLB+) planted in St. Cloud, Florida, making up to 11.5 brix 6-8 weeks prior to expected harvest date (Table 1). This is important, as there has been a brix crisis in both 'Hamlin' (not patented) and 'Valencia' (not patented) juice statewide in Florida the past two seasons, with juices from both oranges averaging less brix than what is needed for Grade A standard NFC juice. Combined with the right rootstock, young trees of 'OLL-DC-3-40' are capable of making Grade A level juice. 'OLL-DC-3-40' trees grow faster and larger than trees of 'Valencia', and 'OLL-DC-3-40' appears to be slightly more vigorous than sibling clone 'OLL-DC-3-36' (provisional plant patent App. No. 63/717,552) (Table 2). The added vigor delayed heavy fruit set during the 2024 harvest, but the crop this season is comparable to that of 'OLL-DC-3-36'. For the 2024 harvest, fruit of both 'OLL-DC-3-36' and 'OLL-DC-3-40' passed maturity standards, whereas standard 'Valencia' did not (Table 3).

There are no data supporting long-term field performance or yield of the new cultivar 'OLL-DC-3-40', although numerous young trees observed growing on 'US-942' (not patented) rootstock have set very good crops the past and current season. No obvious tree-debilitating disease problems have been observed in the trees or fruit currently grown, but systematic resistance testing has not been yet explored. Trees of the new cultivar 'OLL-DC-3-40' are susceptible to *Citrus* canker, similar to the mother clone 'OLL-8'. *Citrus* canker lesions have been found on leaves and a few fruit of 'OLL-DC-3-40', suggesting that its canker tolerance is less than that of 'Valencia', and probably more similar to that of 'Hamlin'. Because of its potentially enhanced HLB tolerance, 'OLL-DC-3-40' is suited for widespread planting in Florida.

The new cultivar 'OLL-DC-3-40' can be compared to the commercial cultivars 'OLL-8' and Valencia 'SPB-1-14-19', but is showing better HLB tolerance. OLL clones have higher brix and color scores than standard Valencia, as well as better HLB tolerance.

DESCRIPTION OF THE FIGURES

This new sweet orange cultivar 'OLL-DC-3-40' is illustrated by the accompanying photographs which show the tree's from, foliage and fruit. The colors shown are as true as can be reasonably obtained by conventional photographic procedures. The photographs are of a tree approximately 4 years old.

DETAILED BOTANICAL DESCRIPTION OF THE CULTIVAR

Figure 1:
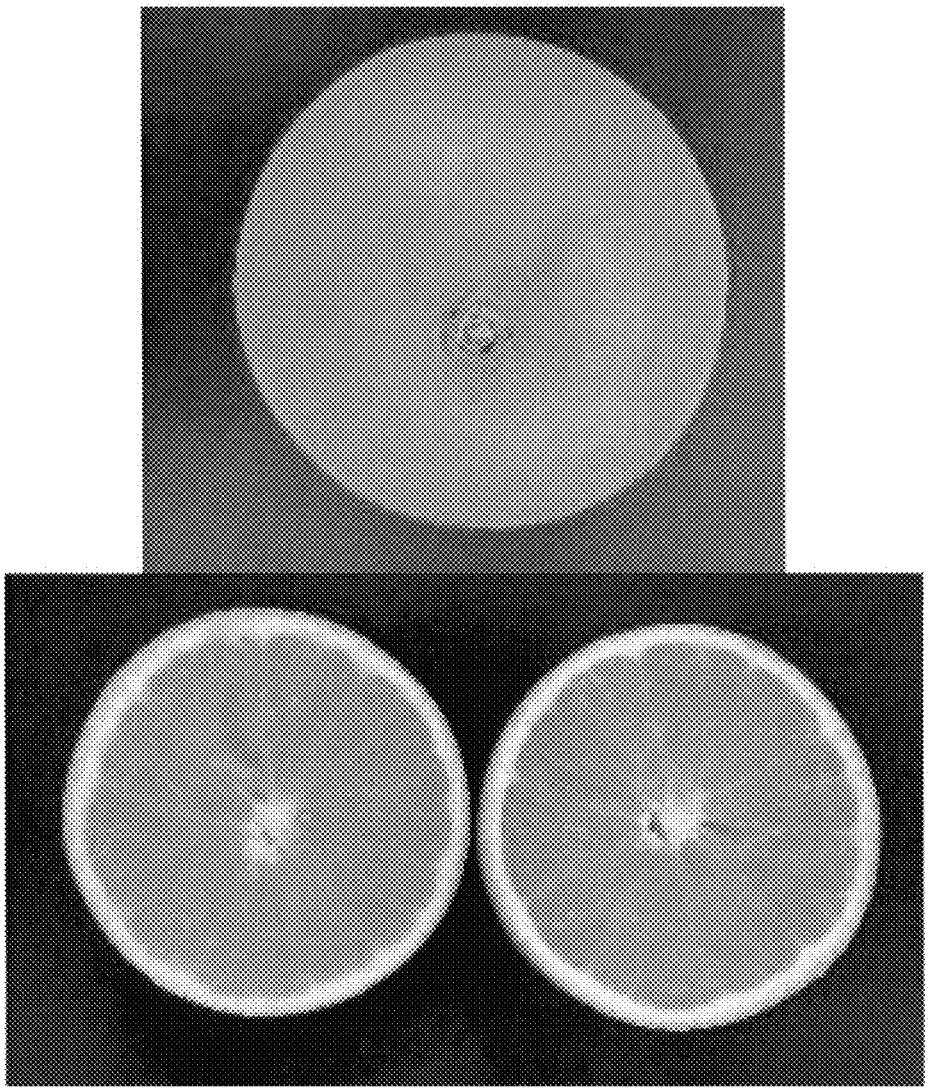
FIG. 1 shows a close-up view of the mature fruit from the new cultivar 'OLL-DC-3-40' with the rind present and cross-sectional view of the fruit when cut in the center.
Figure 2:
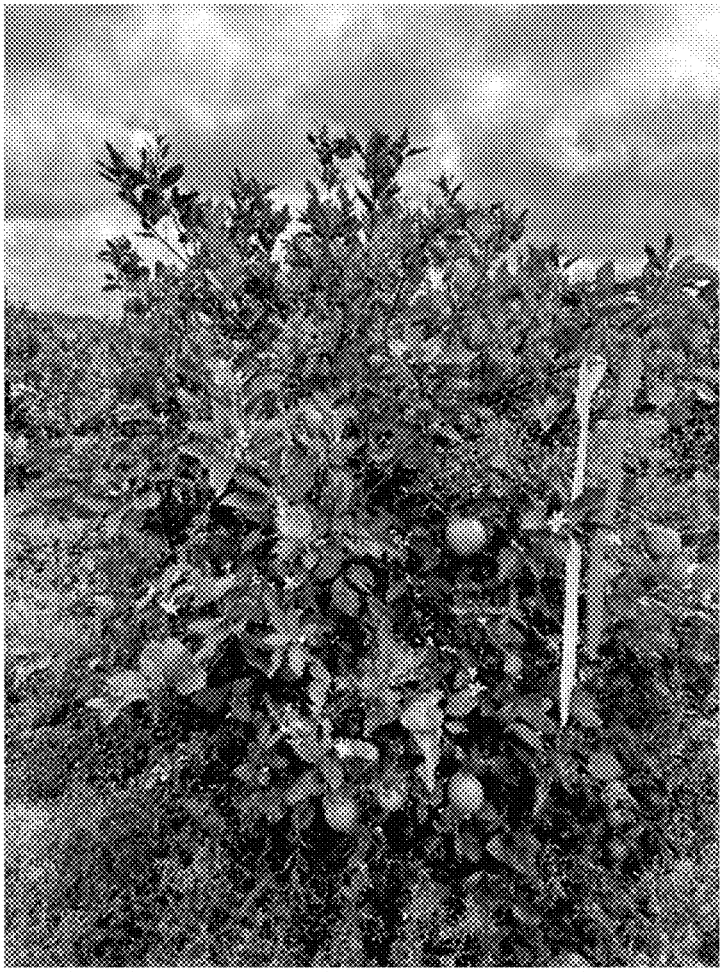
FIG. 2 shows overall tree growth habit of the new cultivar 'OLL-DC-3-40'.
Figure 3:
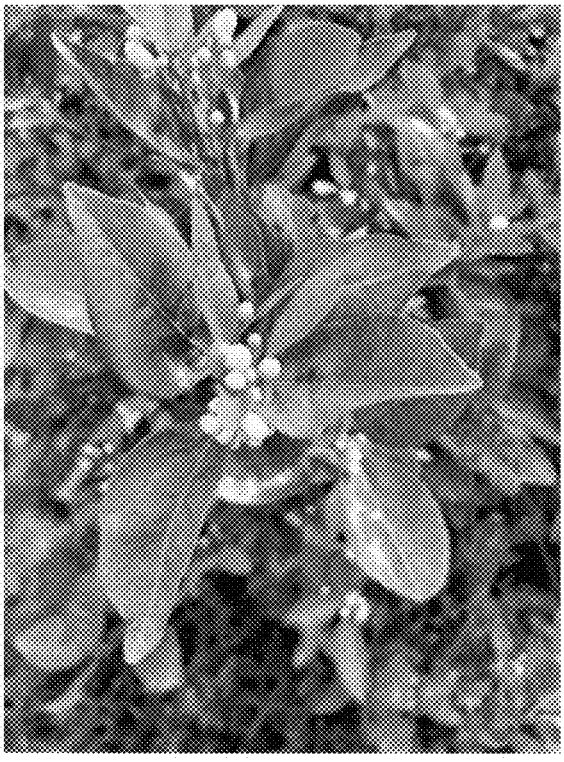
FIG. 3 shows a cluster with flower buds of the new cultivar 'OLL-DC-3-40' in different growth stages.
Figure 4:
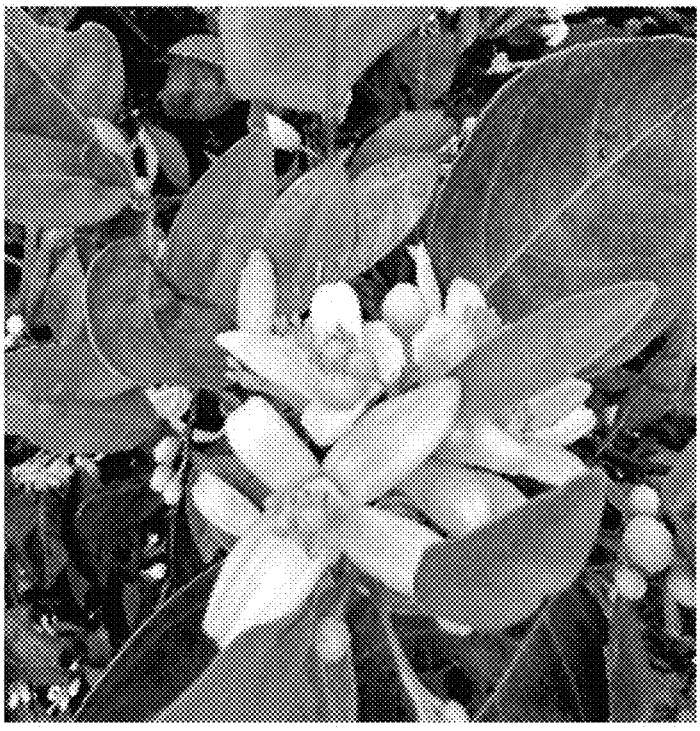
FIG. 4 shows a cluster with flowers of the new cultivar 'OLL-DC-3-40'.
Figure 5:
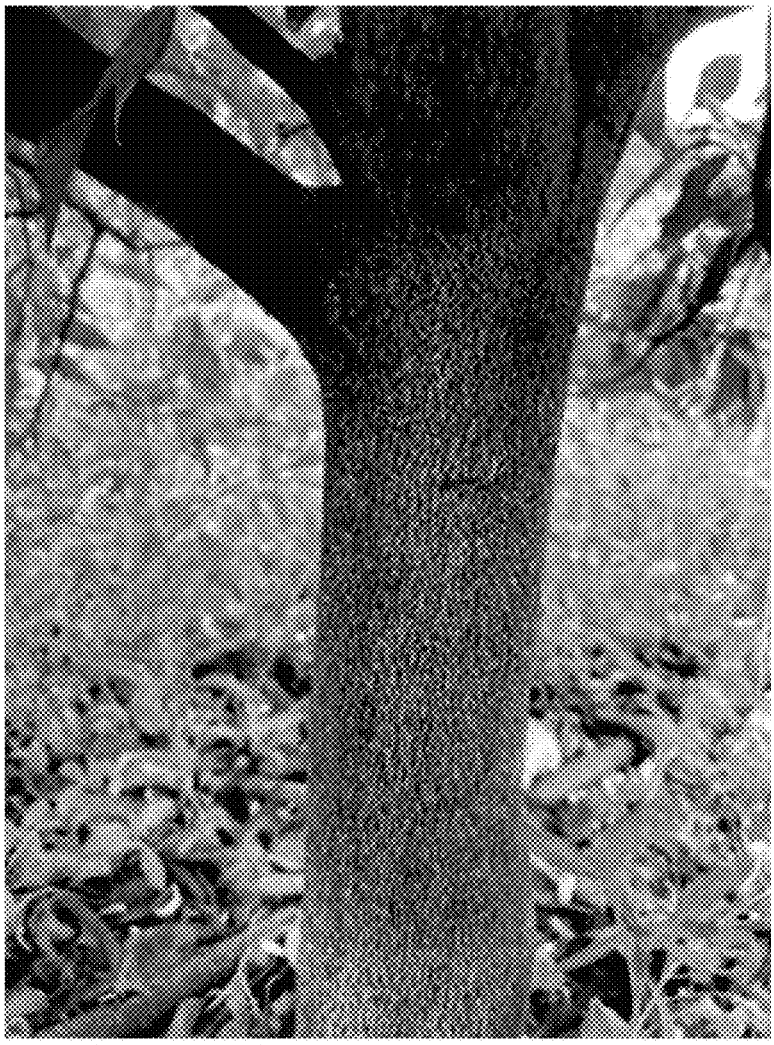
FIG. 5 shows a trunk of a 4.5-year-old tree of the new cultivar 'OLL-DC-3-40'.
Figure 6:
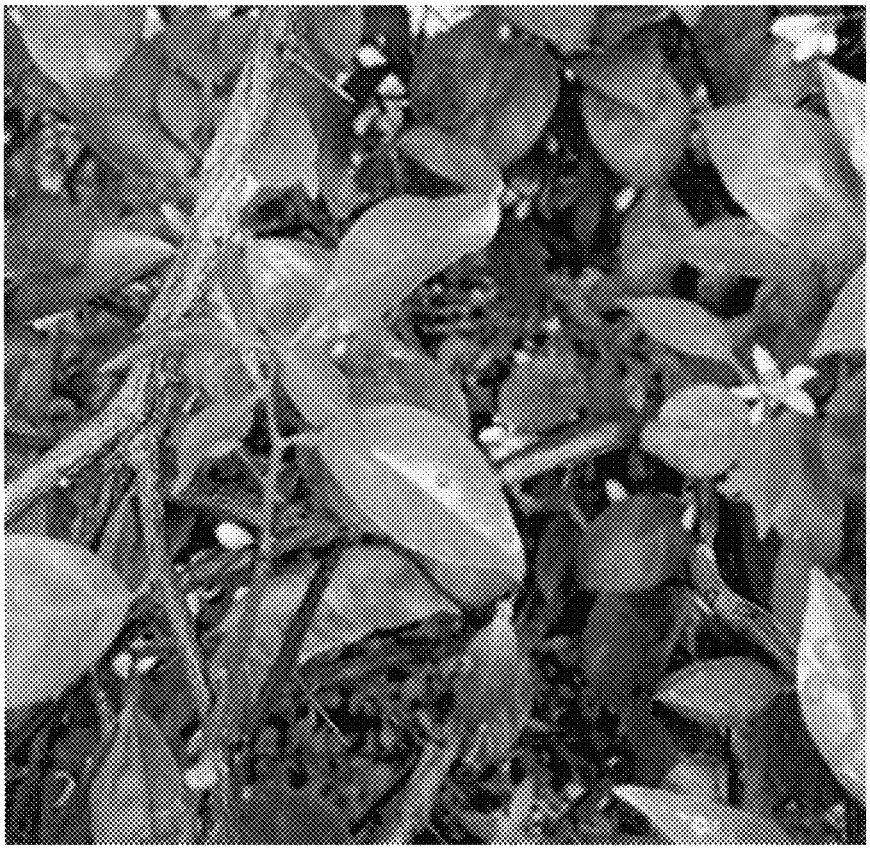
FIG. 6 shows branches of a tree of the new cultivar 'OLL-DC-3-40'.
Figure 7:
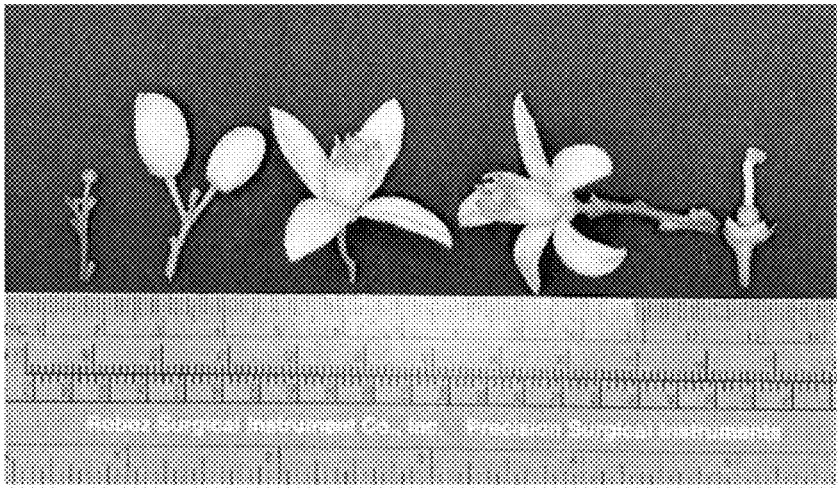
FIG. 7 shows different growth stages of flowers of the new cultivar 'OLL-DC-3-40' with a ruler for size reference.
Figure 8:
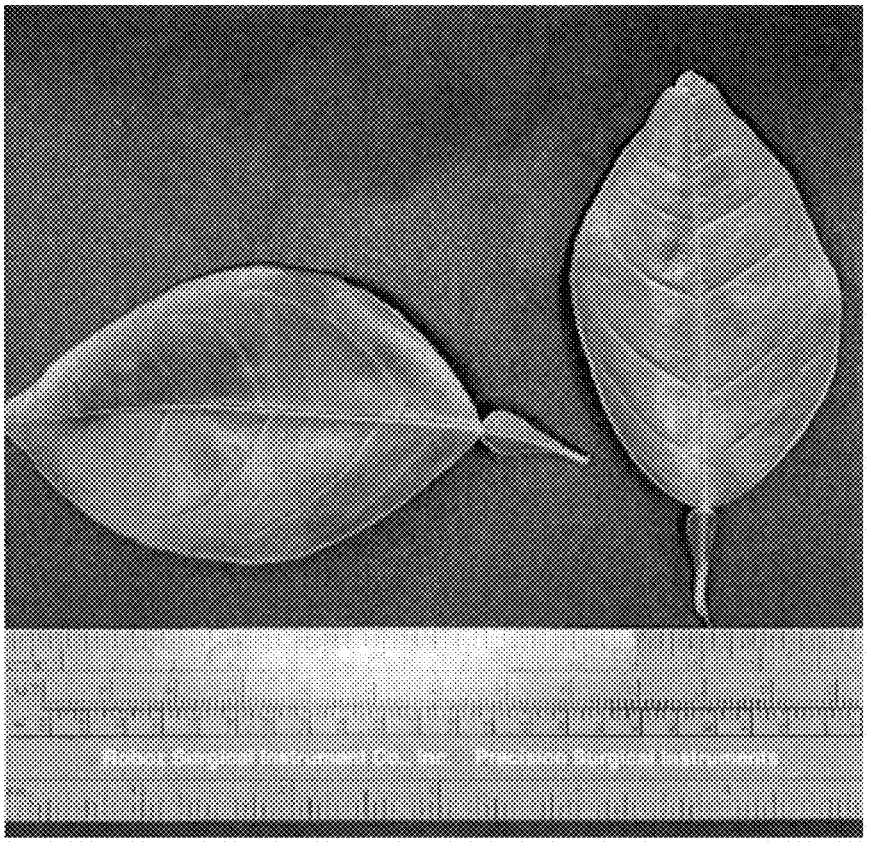
FIG. 8 shows fully expanded leaves of the new cultivar 'OLL-DC-3-40' with a ruler for size reference.
Figure 9:
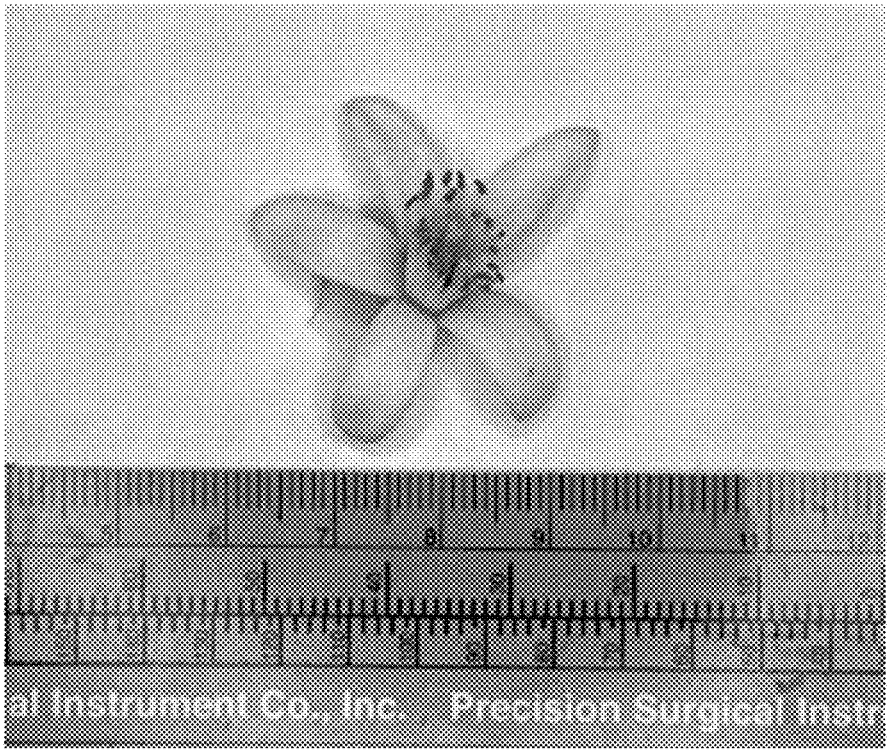
FIG. 9 shows a close-up view of a fully expanded flower of the new cultivar 'OLL-DC-3-40' with a ruler for size reference.
Figure 10:
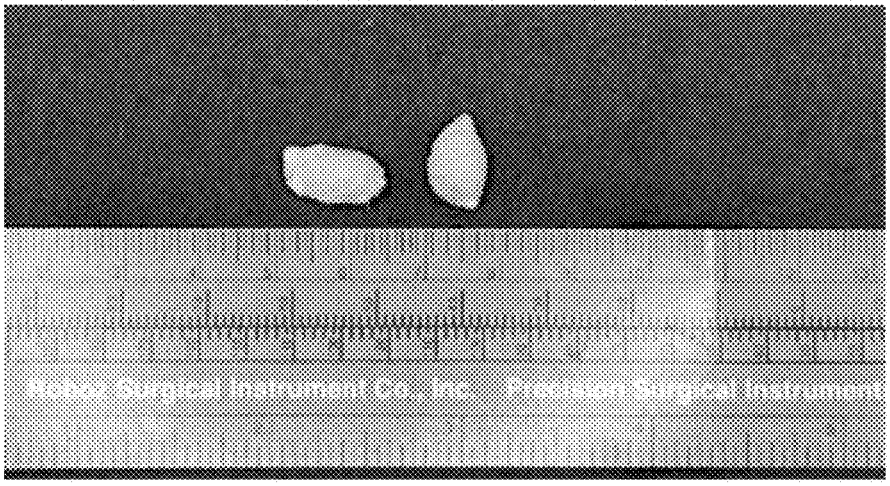
FIG. 10 shows a close-up view of seeds of the new cultivar 'OLL-DC-3-40' with a ruler for size reference.
Figure 11:
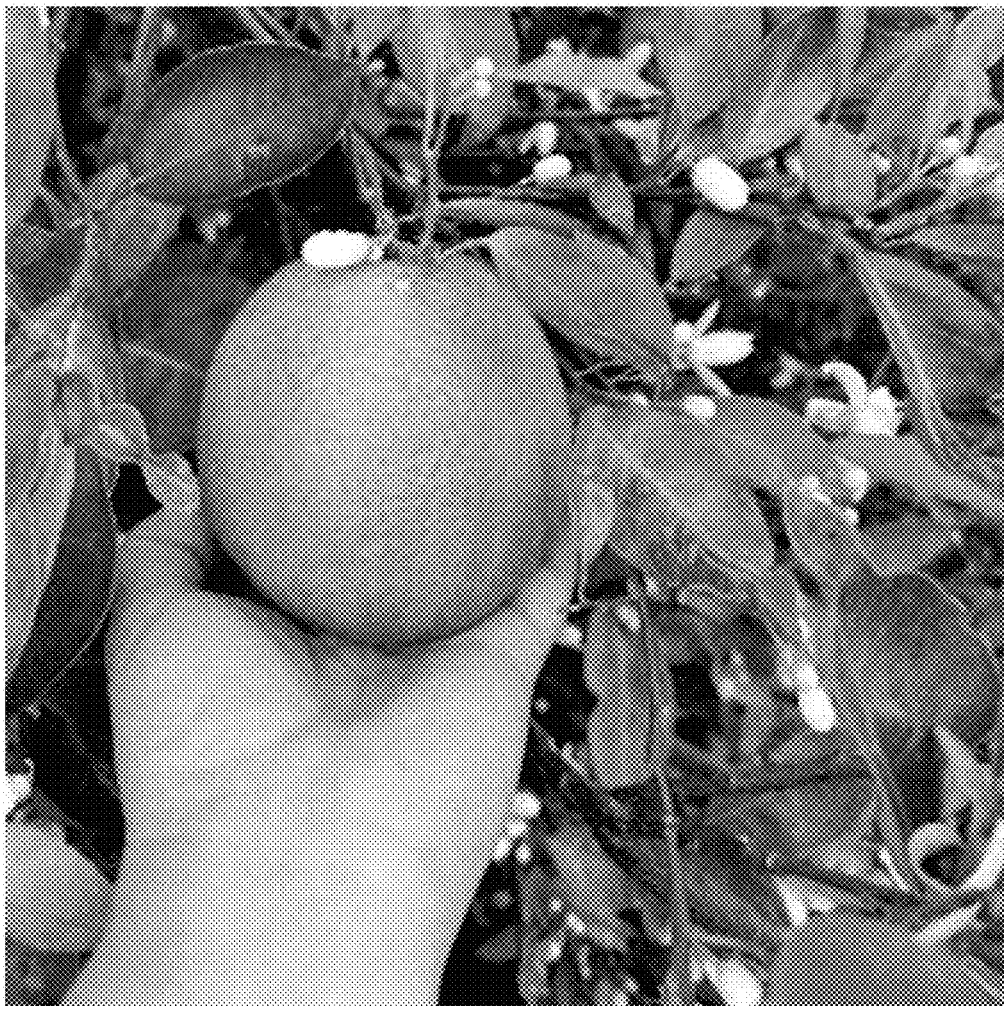
FIG. 11 shows a fruit on a tree of the new cultivar 'OLL-DC-3-40', the fruit not being fully ripe.
Figure 12:
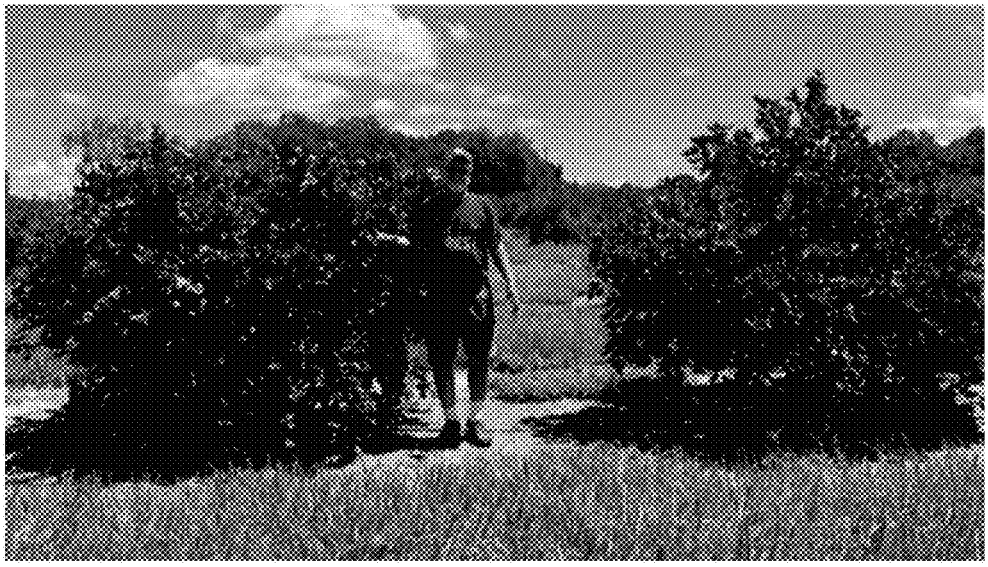
FIG. 12 shows 'OLL-DC-3-40' reset trees growing on 'Fast Eddy' ('UFR-1' clone #28) rootstock, grown with no psyllid control.
Figure 13:
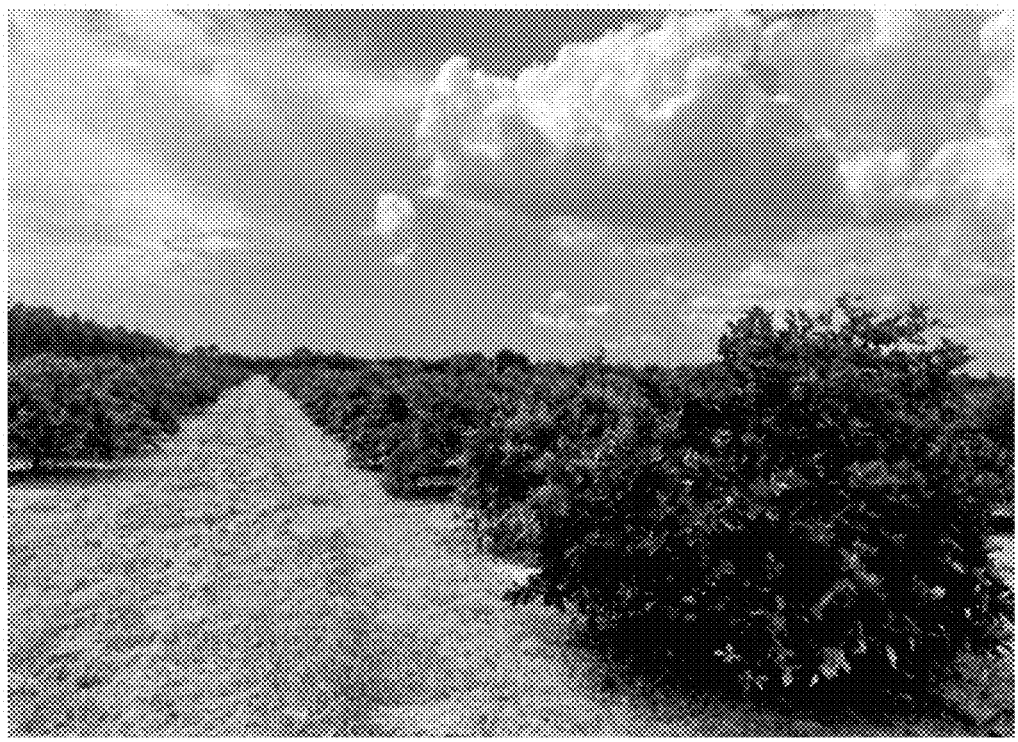
FIG. 13 shows 4.5-year-old trees of the new cultivar 'OLL-DC-3-40' growing on 'US-942' rootstock at Eagle Lake, grown with no individual protective covers (IPCs) and no antibiotics.

The present botanical description is that of the new cultivar 'OLL-DC-3-40' grown on 4.5-year-old trees growing on 'US-942' rootstock (*C. reticulata* x *Poncirus trifoliata*) in Lake Alfred, Florida. The colors (except those in common terms) are described from R.H.S. Colour Chart published by The Royal Horticultural Society in London (2007, 5th edition), in association with the Flower Council of Holland.

Botanical Description

Botanical classification:

*Family*.—Rutaceae.

*Botanical name*.—*Citrus sinensis*.

*Common name*.—Sweet orange.

*Cultivar*.—'OLL-DC-3-40'.

Parentage: OLL (Orie & Louise Lee) Sweet Orange #8 ('OLL-8').

Tree:

*Ploidy*.—Diploid.

*Size*.—Medium.

*Width across the row*.—2.9 meters on average.

*Width down row*.—3 meters on average.

*Tree height*.—2.03 meters on average.

*Tree canopy diameter*.—8.32 meters on average.

*Vigor*.—Vigorous.

*Density*.—Dense.

*Tree shape* (*form*).—Obloid.

*Growth habit* (*current season*).—Drooping.

Trunk:

*Trunk diameter*.—27 cm on average at 30 cm above the ground.

*Trunk texture*.—Rough with vertical strips.

*Trunk bark color*.—RHS 197A (Grey-Brown Group).

Branches:

*Branch length*.—1.37 meters on average.

*Branch diameter*.—11.81 cm on average.

*Crotch angle*.—On average, the angle is less than 90 degrees in the middle of the tree and some crotch angles on the outside are more than 90 degrees.

*Branch texture*.—Relatively smooth and with small thorns.
*Branch color*.—RHS 199A (Grey-Brown Group).
*Thorns*.—Length: 25 mm on average. Density: 3 per foot on average.

Leaves:
Size (lamina average):
*Length*.—82 mm on average.
*Width*.—48 mm on average.
*L/W ratio*.—1.71 on average.
*Thickness*.—Regular (approximately 0.25 mm).
*Type*.—Simple (unifoliate).
*Shape*.—Elliptical.
*Apex*.—Slightly retuse.
*Base*.—Acute to sub-obtuse.

Surface:
*Upper surface*.—Glabrous.
*Lower surface*.—Smooth texture with a lack of indentations, projections, trichomes, or rough surface growths.

Color:
*Upper surface* (*adaxial*).—RHS 138A (Green Group).
*Lower surface* (*abaxial*).—RHS 146 D (Yellow-Green Group).

Petiole:
*Shape and attachment*.—Brevipetiolate. The junction between petiole and lamina is articulate.
*Shape* (*petiole wing*).—Obovate with narrow end at the base.
*Length*.—18 mm on average.
*Width*.—4.5 mm on average.
*Color*.—*RHS* 144 A (Yellow-Green Group).

Flowers:
*Type*.—Hermaphrodite.
*Flowers bearing*.—Flowers grow from leaf terminals and leaf axillaries. Some branches have flower grown in clusters, each cluster consists of 2 to 6 flowers. Some flowers can grow individually.
*Flower diameter*.—34 mm on average.
*Flower depth*.—14 mm on average.
*Flower blooming period*.—*February to April*.
*First bloom*.—Late February.
*Full bloom*.—March.
*Fragrance*.—Fragrant.

Flower buds' size:
*Length*.—1.4 mm on average for the initially visible flower bud; 12.5 mm on average in the mature bud.
*Diameter*.—1.3 mm on average in the initial visible flower bud; 9.3 mm on average in the matured bud.
*Flower bud shape*.—Initially with a round shape and having an elongated olive shape when mature.
*Flower bud color* (*RHS*).—RHS 144C (Yellow-Green Group) for the initial visible flower bud; RHS 157B (Green-White Group) for mature buds.
*Fertility*.—Appears to be self-fertile.

Petals:
*Number*.—5.
*Petal length*.—18.2 mm on average.
*Petal width*.—7.3 mm on average.
*Petal shape*.—Recurved/cruciform.
*Apex shape*.—Smooth with an obtuse angle.
*Base shape*.—Obtuse.

Petal color:
*Upper surface*.—RHS 155A (White Group).
*Lower surface*.—RHS 155B (White Group).
*Margin*.—Smooth.

Sepal:
*Number* (*per flower*).—4 per flower on average.
*Shape*.—Short flat delta with acute angle at apex.
*Length*.—4.4 mm on average.
*Width*.—4.5 mm on average.
*Apex shape*.—Acute.
*Margin*.—Smooth.

Sepal color:
*Upper surface*.—RHS 145C (Yellow-Green Group).
*Lower surface*.—RHS 144D (Yellow-Green Group).

Pedicel:
*Length*.—6.7 mm on average.
*Diameter*.—1.5 mm on average.
*Color*.—RHS 144 C (Yellow-Green Group).

Stamen:
Number.—28 per flower on average.
Length.—13.4 mm on average.

Anther:
*Length*.—1.9 mm on average.
*Width*.—0.8 mm on average.
*Pollen color* (*general*).—RHS 163A (Greyed-Yellow Group).

Pistil:
*Number*.—1.
*Length*.—9.6 mm on average.
*Color*.—RHS 145C (Yellow-Green Group).
*Style length*.—7.2 mm on average.
*Style diameter*.—1.9 mm on average.
*Style color RHS*.—RHS 145C (Yellow-Green Group).
*Ovary shape*.—Oval.
*Ovary diameter*.—2.9 mm on average.
*Ovary color*.—RHS 144A (Yellow Green Group).

Fruit:
*Fruit weight*.—130-150 g on average.
*Size*.—Uniform (small to medium size). Diameter: 65 mm on average. Length: 70 mm on average.
*Shape*.—Round and earth-shaped.
*Shape* (*cross-section*).—Round.
*Apex*.—Truncated with shallow dent mark.
*Base*.—Truncated with smooth areola.

Rind:
*Adherence*.—Albedo (mesocarp) to fresh (endocarp) is strong and relatively difficult to separate.
*Thickness*.—Approximately 3 mm to 4 mm, thin to medium compared to other commercial sweet orange varieties.
*Texture*.—Firm.
*Color*.—Flavedo (epicarp): RHS 16A (Yellow-Orange Group) when the fruit is totally mature. Albedo (mesocarp): RHS 18D (Yellow-Orange Group). Endocarp: RHS 25B (Orange Group).
*Stylar end*.—Closed.
*Oil cell density*.—Approximately 78 per $mm^2$.
*Fruit surface*.—Pitting and pebbling absent.
*Core diameter*.—3 mm on average.
*Filing of the core*.—Very sparse. Almost entirely flesh-filled center, often with no distinct core membrane or empty space.

Flesh:
*Number of segments*.—9 to 10 segments per fruit on average.
*Segment walls*.—Soft, but of sufficient strength to maintain integrity as separated.

*Juice*.—Abundant.

*Color*.—Uniformly colored RHS 25B (Orange Group) (USDA orange juice color system score of 39.9).

*Texture*.—Soft.

*Segments*.—Segment length: 66 mm on average. Segment diameter: 13 mm on average.

*Vesicles*.—Medium thickness. Length: 7 mm on average. Width: 2.5 mm on average.

Eating quality:

*Sucrose content* (*average Brix*).—9.5-11.5 (in young trees, approximately 3-5 years of age, with HLB).

*Acidity*.—0.97 on average (in young trees with HLB).

*Sugar*:acid ratio.—12 (in young trees with HLB; higher brix and ratio are expected if harvested later or from older trees).

Seeds:

*Type*.—Polyembryonic.

*Number*.—Between 3 to 4 seeds (3.9 on average).

*Shape*.—Variable, typically clavate/club shaped to deltoid shaped.

*Size*.—Length: 15 mm on average. Width: 7 mm on average.

*Seed coat color*.—Outer Surface: RHS 163D (Greyed-Orange Group). Inner surface: RHS 165D (Greyed-Orange Group). Cotyledon color: RHS 157A (Green-White Group).

TABLE 1

Juice quality data from 3.5-year-old reset trees of 'OLL-DC-3-40', as well as other OLL series clones, from oranges harvested in January 2023 from St. Cloud, Florida (6-8 weeks prior to expected full maturity).

Data:

| Sample ID | Scion/rootstock | Wt. Sample (lbs.) | Wt. Juice (lbs.) | Wt. Juice per Box (lbs.) | % Acid | Total ° Brix | Ratio | Lbs. Solids per Box | Juice Color |
|---|---|---|---|---|---|---|---|---|---|
| R1T9 | 'OLL-DC-3-40'/'UF-1' CL.55 'Super Roots' | 4.54 | 2.58 | 51.145 | 1.50 | 11.50 | 7.67 | 5.88 | 36.8 |
| RIT11 | 'OLL-3-IR' 46x '20-04-42' | 11.07 | 6.41 | 52.114 | 1.31 | 10.26 | 7.83 | 5.35 | 36.2 |
| RIT12 | 'OLL-DC-3-36'/'UF-1' CL.55 'Super Roots' | 4.96 | 2.97 | 53.891 | 1.15 | 11.30 | 9.83 | 6.09 | 37.1 |
| R1T13 | 'OLL-DC-3-40'/'UF-1' CL.28 'Fast Eddy' | 2.99 | 1.57 | 47.258 | 1.25 | 10.40 | 8.32 | 4.92 | 35.5 |
| R2T6 | 'OLL-DC-3-40'/'UF-1' CL.2 'Super Roots-2' | 17.20 | 9.97 | 52.169 | 1.06 | 10.06 | 9.49 | 5.25 | 37.3 |
| R2T14 | 'OLL-DC-3-40'/'UF-1' CL.28 'Fast Eddy' | 5.81 | 3.41 | 52.823 | 0.97 | 10.10 | 10.41 | 5.33 | 36.7 |
| R2T15 | 'OLL-DC-3-36'/'UF-1' CL.28 'Fast Eddy' | 4.81 | 2.80 | 52.391 | 1.17 | 10.70 | 9.15 | 5.61 | 36.1 |
| R2T16 | 'OLL-DC-3-36'/'UF-1' CL.55 'Super Roots' | 12.40 | 7.35 | 53.347 | 1.38 | 11.92 | 8.64 | 6.36 | 36.3 |
| R4T1 | 'OLL-DC-3-36'/'UF-1' CL.2 'Super Roots-2' | 13.22 | 7.59 | 51.672 | 1.04 | 10.20 | 9.81 | 5.27 | 36.7 |
| R7T28 | 'OLL-DC-3-36'/'UF-1' CL.2 'Super Roots-2' | 18.28 | 10.55 | 51.942 | 1.24 | 10.72 | 8.65 | 5.57 | 36.3 |

Trees were HLB+ and grown with no psyllid control.

TABLE 2

Comparison of 4-year-old trees of 'OLL-DC-3-40' grown on 'US-942' rootstock ('OLL-DC-3-40'/'US-942'), 'OLL-DC-3-36' grown on 'US-942' ('OLL-DC-3-36'/'US-942'), and 'Valencia' grown on 'US-942' rootstock ('Valencia'/'US-942') for tree size and yield, average of 10 trees per selection (data collected February 2024).

| Scion/ Rootstock | | Tree Height (m) Mean* | Scion/ Rootstock | | Tree Canopy Volume (m) Mean* | Scion/ Rootstock | | Boxes/ Tree Mean* |
|---|---|---|---|---|---|---|---|---|
| 'OLL-DC-3-40'/ 'US-942' | A | 2.0 | 'OLL-DC-3-40'/ 'US-942' | A | 9.3 | 'OLL-DC-3-36'/ 'US-942' | A | 0.4 |
| 'OLL-DC-3-36'/ 'US-942'' | A | 1.9 | 'OLL-DC-3-36'/ 'US-942' | A | 7.9 | 'OLL-DC-3-40'/ 'US-942' | B | 0.1 |
| 'Valencia'/ 'US-942' | B | 1.4 | 'Valencia'/ 'US-942' | B | 5.4 | 'Valencia'/ 'US-942' | B | 0.1 |

*Means not connected by the same letter are significantly different ($\alpha = 0.05$).

TABLE 3

Pilot Plant Juice Quality Data from OLL clones, including 'OLL-DC-3-40' and 'Valencia', fruit harvested from 4-year-old trees at Eagle Lake, Florida (note that 'Valencia' did not pass maturity standards).

| Sample ID | Wt. Sample (Lbs.) | Wt. Juice (Lbs.) | Lbs. Juice per Box | % Acid | Total ° Brix | Ratio | Bin No. | Lbs. Solids per Box | Juice Color | Avg. Fruit Wt. |
|---|---|---|---|---|---|---|---|---|---|---|
| 'OLL-DC-3-40' Eagle | 17.98 | 10.36 | 51.858 | 0.97 | 9.54 | 9.84 | 46 | 4.95 | 39.39 | 0.39 |
| 'OLL-DC-3-36' Eagle | 18.22 | 10.50 | 51.866 | 0.85 | 9.14 | 10.75 | 43 | 4.74 | 39.10 | 0.44 |
| 'OLL-8' Eagle | 21.30 | 11.79 | 49.817 | 0.96 | 9.41 | 9.80 | 51 | 4.69 | 38.87 | 0.42 |
| 'Valencia' Eagle | 20.38 | 11.19 | 49.416 | 1.14 | 8.93 | 7.83 | 63 | 4.41 | 37.33 | 0.32 |

The invention claimed is:

1. A new and distinct sweet orange plant named 'OLL-DC-3-40' as illustrated and described herein.

* * * * *